(12) United States Patent
Rowney et al.

(10) Patent No.: US 9,480,717 B2
(45) Date of Patent: Nov. 1, 2016

(54) COMPOSITION OF WHEY GROWTH FACTOR EXTRACT FOR REDUCING MUSCLE INFLAMMATION

(75) Inventors: Michelle Rowney, Port Campbell (AU); David Cameron-Smith, Ashburton (AU)

(73) Assignee: Murray Goulburn Co-Operative Co Limited, Brunswick (AU)

( * ) Notice: Subject to any disclaimer, the term of this patent is extended or adjusted under 35 U.S.C. 154(b) by 0 days.

(21) Appl. No.: 13/602,864

(22) Filed: Sep. 4, 2012

(65) Prior Publication Data

US 2013/0195990 A1    Aug. 1, 2013

Related U.S. Application Data (63) Continuation of application No. 11/991,696, filed as application No. PCT/AU2006/001323 on Sep. 8, 2006, now abandoned.

(30) Foreign Application Priority Data

Sep. 9, 2005   (AU) ............................... 2005904980

(51) Int. Cl.
  *A61K 35/20*   (2006.01)
  *A23C 21/06*   (2006.01)
  *A23J 1/20*    (2006.01)
  *A23L 1/305*   (2006.01)
  *A61K 38/17*   (2006.01)
  *A23L 1/29*    (2006.01)

(52) U.S. Cl.
  CPC .............. *A61K 35/20* (2013.01); *A23C 21/06* (2013.01); *A23J 1/205* (2013.01); *A23L 1/296* (2013.01); *A23L 1/3056* (2013.01); *A61K 38/1709* (2013.01); *A23V 2002/00* (2013.01); *A23V 2300/30* (2013.01)

(58) Field of Classification Search
  None
  See application file for complete search history.

(56) References Cited

U.S. PATENT DOCUMENTS

| | | | |
|---|---|---|---|
| 6,019,999 A | 2/2000 | Miller et al. | |
| 6,475,511 B2 | 11/2002 | Gohlke et al. | |
| 6,784,209 B1 | 8/2004 | Gardiner et al. | |
| 8,282,927 B2 | 10/2012 | Brown et al. | |
| 2002/0001625 A1* | 1/2002 | Ballard et al. | 424/535 |
| 2002/0006907 A1* | 1/2002 | Gardiner | A23L 1/296 514/5.6 |
| 2004/0071825 A1* | 4/2004 | Lockwood | 426/72 |
| 2005/0153019 A1 | 7/2005 | Fuchs et al. | |
| 2009/0169675 A1 | 7/2009 | Rowney et al. | |
| 2009/0324733 A1 | 12/2009 | Rowney et al. | |
| 2013/0078313 A1 | 3/2013 | Rowney et al. | |

FOREIGN PATENT DOCUMENTS

| | | |
|---|---|---|
| CA | 2537647 A1 | 9/2006 |
| EP | 0064103 A1 | 11/1982 |
| EP | 0545946 B1 | 6/1993 |
| EP | 0869134 B1 | 10/1998 |
| JP | 5-139990 | 3/1993 |
| JP | 5-508542 | 12/1993 |
| JP | 7-267995 | 10/1995 |
| JP | 2002-65212 | 3/2002 |
| JP | 2002-513544 | 5/2002 |
| JP | 2004-182630 | 7/2004 |
| JP | 2005-289861 | 10/2005 |
| SU | 1507790 | 9/1989 |
| WO | 92/00994 A1 | 1/1992 |
| WO | 99/56758 A1 | 11/1999 |
| WO | 01/56402 A2 | 8/2001 |
| WO | 02/15720 A2 | 2/2002 |
| WO | 2004/034986 A2 | 4/2004 |
| WO | 2004/049830 A1 | 6/2004 |
| WO | 2007/028210 A1 | 3/2007 |
| WO | 2007/028211 A1 | 3/2007 |

OTHER PUBLICATIONS

Tran et al. Am J Clin Nutr May 2003 vol. 77 No. 5 1296-1303.*
Doultani et. al. "Fractionastion of Proteins from Whey using cation exchange chromatography". Process Biochemistry. vol. 39 (2004) 1737-1743.*
Anderson, Judy E. et al., "Satellite cell activation on fibers: modeling events in vivo—an invited review," Can. J. Physiol. Pharmacol., vol. 82:300-310 (2004).
Andersen, Lars L. et al., "The effect of resistance training combined with timed ingestion of protein on muscle fiber size and muscle strength," Metabolism Clinical and Experimental, vol. 54:151-156 (2005).
Bodybuilding.com, "TNT presents: Isolate-X, Purest Protein Fractions Available!" retrieved from http://www.bodybuilding.com/store/tnt/iso.html, 1 page (2002).
Boucher, Jeremie et al., "Insulin and Insulin-like Growth Factor-1 Receptors Act as Ligand-specific Amplitude Modulators of a Common Pathway Regulating Gene Transcription," The Journal of Biological Chemistry, vol. 285 (22):17235-17245 (2010).
Bruning, Jens C. et al., "Ribosomal subunit kinase-2 is required for growth factor-stimulated transcription of the c-Fos gene," PNAS, vol. 97(6):2462-2467 (2000).
Burke, Darren G. et al., "The Effect of Whey Protein Supplementation With and Without Creatine Monohydrate Combined With Resistance Training on Lean Tissue Mass and Muscle Strength," International Journal of Sport Nutrition and Exercise Metabolism, vol. 11:349-364 (2001).

(Continued)

*Primary Examiner* — Amy L Clark
(74) *Attorney, Agent, or Firm* — Nelson Mullins Riley & Scarborough LLP; Amy E. Mandragouras, Esq.; Erika L. Wallace (57) ABSTRACT

The invention relates to the production of compositions containing milk products for use as a nutritional supplement. More specifically, it relates to compositions containing whey growth factor extract, as well as their use in methods for reducing muscle inflammation in individuals undertaking resistance exercise training. According to one aspect of the invention, there is provided the use of a composition comprising whey growth factor extract, isolated from a milk product by cation exchange chromatography, to reduce exercise-induced muscle inflammation.

18 Claims, 8 Drawing Sheets

(56) References Cited

OTHER PUBLICATIONS

CAplus AC 2005-204816, Sgarbieri, Valdemiro Carlos, "Physiological and functional properties of milk whey proteins," Revista de Nutricao, vol. 17(4):397-409 (2004).
Cornelison, D.D.W. et al., "Syndecan-3 and Syndecan-4 Specifically Mark Skeletal Muscle Satellite Cells and Are Implicated in Satellite Cell Maintenance and Muscle Regeneration," Developmental Biology, vol. 239:79-94 (2001).
Holly, Cory, "The Right Whey Protein," retrieved online at http://www.coryholly.com/articles/article.cfm?id=58, 4 pages, (2004).
MacIntyre, Donna L. et al., "Delayed Muscle Soreness, The Inflammatory Response to Muscle Injury and its Clinical Implications," Sports Med., vol. 20(1):24-40 (1995).
MacIntyre, Donna L. et al., "Markers of inflammation and myofibrillar proteins following eccentric exercies in humans," Eur. J. Appl. Physiol., vol. 84:180-186 (2001).
Seale, Patrick et al., "Muscle satellite cell-specific genes identified by genetic profiling of MyoD-deficient myogenic cell," Developmental Biology, vol. 275:287-300 (2004).
Tipton, Kevin D. et al., "Ingestion of Casein and Whey Proteins Result in Muscle Anabolism after Resistance Exercie," Medicine & Science in Sports & Exercise, vol. 36(12):2073-2081 (2004).
Urban Biologics, "Isolate-X—2 lb. Tub," retrieved online at http://www.urbanbiologics.com/prod.itml/icOid/7, 2 pages, (2006).
International Search Report for Application No. PCT/AU2006/001322, 5 pages, dated Dec. 5, 2006.
International Search Report for Application No. PCT/AU2006/001323, 4 pages, dated Dec. 5, 2006.
Davis, J.M. et al., "Animal Model of Performance Enhancement by Nutritional Supplements with Anti-inflammatory Activity," Proceedings 24th Army Science Conference, pp. 1-5 (2004).
Francis, G.L. et al., "Extraction from Cheese Whey by Cation-Exchange Chromatography of Factors that Stimulate the Growth of Mammalian Cells," J. Dairy Sci., vol. 78:1209-1218 (1995).
Ha, Ewan et al., "Functional properties of whey, whey components, and essential amino acids: mechanisms underlying health benefits for active people (Review," Journal of Nutritional Biochemistry, vol. 14:251-258 (2003).
Natra Range, "NatraPro: Caselns," MG Nutritionals, 6 pages (2004).
Spies, M. et al., "Liposomal IGF-1 gene trasfer modulates pro- and anti-inflammatory cytokine mRNA expression in the burn wound," Gene Therapy, vol. 8:1409-1415 (2001).
Australian Office Action for Application No. 2006289666, 4 pages, dated May 27, 2011.
Korean Office Action for Application No. 7008517/2008, 11 pages, dated Mar. 28, 2014.
Japanese Office Action for Application No. 2013-076719, 6 pages, dated May 21, 2014.
International Preliminary Report on Patentability and Written Opinion for Application No. PCT/AU2006/001323, 7 pages, dated Mar. 11, 2008.
Canadian Office Action, Canadian Application No. 2,621,739, dated Apr. 8, 2015, 4 pages.
Ye, X. et al., Isolation of lactoperoxidase, lactoferrin, a-lactalbumin, b-lactoglobulin B and b-lactoglobulin A from bovine rennet whey using ion exchange chromatography, The International Journal of Biochemistry & Cell Biology, vol. 32 1143-1150 (2000).

* cited by examiner

COMPOSITION OF WHEY GROWTH FACTOR EXTRACT FOR REDUCING MUSCLE INFLAMMATION

RELATED APPLICATIONS

This application is a continuation of U.S. Ser. No. 11/991,696, filed on Sep. 2, 2009 (Pending), which is a 35 U.S.C. §371 national stage filing of PCT Application No. PCT/AU2006/001323 filed on Sep. 8, 2006, which claims priority to AU Application No. 2005904980 filed on Sep. 9, 2005. The contents of the aforementioned applications are hereby incorporated by reference.

FIELD OF THE INVENTION

The invention relates to the production of compositions containing milk products for use as a nutritional supplement. More specifically, it relates to compositions containing whey growth factor extract, as well as their use in methods for reducing muscle inflammation in individuals undertaking resistance exercise training.

BACKGROUND OF THE INVENTION

The present invention is to be understood in light of what has previously been done in the field. However, the following discussion is not an acknowledgement or admission that any of the material referred to was published, used or part of the common general knowledge in Australia as at the priority date of the application.

The use of nutritional supplements by humans, and even animals, to improve general health or to improve, for example, athletic performance, is known. Nutritional supplements are not intended to provide all the nutrients necessary for a complete diet, but instead are generally intended to complement the dietary intake such that it becomes more nutritionally complete. It is recognised that vitamins, minerals and other substances found in such supplements play important physiological roles and that a deficiency of certain vitamins, minerals and/or other components of supplements has been linked to development of certain diseases, a decrease in general health or lower performance in athletes.

Conversely, nutritional supplements are known to enhance a variety of physiological states, under various conditions. There are many targets for nutritional supplements, for example sick patients, convalescing patients, elderly persons and persons undergoing strenuous exercise regimes who wish to improve their performance and/or recovery from such exercise.

The nutritional requirements of bodybuilders and persons engaged in strenuous physical exercise are quite particular, whether to decrease body fat and increase lean muscle mass, and or to improve recovery from the strenuous exercise. Recovery includes the ability to overcome exercise-induced inflammation.

Inflammation is a localised response to injury or destruction of tissues. It is characterised in the acute form by pain, heat, redness, swelling, and loss of function. Accordingly, reduced muscle inflammation includes, but is not limited to a reduction in any one or more of the aforementioned symptoms in muscle. The inflammatory response antagonises muscle protein synthesis and contributes to much of the physical discomfort experienced by persons 1 to 2 days after engaging in strenuous exercise, including resistance exercise training (MacIntyre D L, et al., Sports Med. 1995; 20(1):24-40; MacIntyre D L, et al., Eur J Appl Physiol. 2001; 84(3):180-6). If the inflammation is severe, anti-inflammatory drugs such as corticosteroids may be prescribed. However, the use of such drugs can have deleterious side-effects and, in many cases, is prohibited for athletes in competition.

Weight-bearing or resistance training exercise elicits a wide-range of responses in the activated muscle. There are anabolic signalling pathways activated by the stretch and strain of muscles and by growth factors which may be synthesised locally or circulate in the blood stream.

Modulation of the expression of various genes is an essential process in regulating the sequence of cellular events needed to activate stem cells that are located within the muscle bed (satellite cells) (Anderson & Wozniak, Can J Physiol Pharmacol. 2004; 82(5):300-10) to rapidly proliferate, before maturing and ultimately fusing with existing muscle fibres or joining together to create new muscle fibres. Regulators of the activation of satellite cells include Syndecan-3 (a transmembrane heparin sulphate proteoglycan essential for satellite cell proliferation), and Pax-7 (a protein that is essential for satellite cell activation and necessary for muscle tissue repair) (Seale et al., Dev Biol. 2004; 275(2): 287-300; Cornelison et al., Dev Biol. 2001; 239(1):79-94). Other genes involved in the exercise-induced muscle repair and inflammation process include the small molecular weight chemokines (CCL2 and CCL4) and the early response genes, jun-B and c-fos.

If a natural food product, such as a product derived from milk, could be obtained having beneficial effects on exercise recovery it would be a readily available and safe therapeutic supplement.

It is known in the prior art to produce a milk product from cows maintained in a specific hyperimmune state, created by administering periodic booster immunisations with sufficiently high doses of antigens, which can be used to treat various diseases including arthritis, dermatitis and neoplastic diseases (EP 0 064103 A1, Beck L R). Normal cow's milk however does not contain the specific 'anti-inflammatory factor' present in milk produced from the aforementioned hyper-immunised animals, although it is believed to contain low levels of other anti-inflammatory factors. A person of skill in the art would appreciate that production of the anti-inflammatory milk products according to EP 0 064103 A1 is very expensive and time consuming.

It is also known in the prior art to produce anti-inflammatory milk products comprising colostrum which is rich in immunoglobulins. Colostrum is the pre-milk produced immediately after birth before the breast secretions stabilize into milk. Prime colostrum from cows is obtained within the first six hours after calving and contains four times the protein found in milk from the same cow obtained 48 hours later. The immunoglobulin fraction of colostrum is loaded with antibodies, lactoferrin and immune enhancers. Lactoferrin is thought to enhance the anti-inflammatory effect of colostrum, and is the subject of U.S. Pat. No. 6,475,511 (Gohlke M B). Immunoglobulins are thought to act locally on immune function in the gut.

Protein supplementation has been used widely by persons undertaking resistance exercise training to promote muscle protein synthesis in order to repair muscle tissue and facilitate muscle growth. The nutritional supplementation may be provided in the form of a drink or food and includes protein powders to be mixed with liquid for use, nutritional bars and snack foods, tablets, capsules and other preparations. Suitable protein sources commercially available include hydrolysed milk proteins, caseinates, soy protein isolates and milk protein concentrates prepared from ultra-filtrated skim milk. Nutritional supplements which are based on other protein sources, such as whey protein, are also available and can be provided in the form of fruit juices, but are thought to be inadequate because they do not also provide a lipid source (WO 02/15720). In addition, it has been considered that some milk-derived proteins are not readily absorbed by the gut, or do not survive the harsh environment of the digestive system to have a therapeutic effect.

Whey growth factor extract (WGFE) is one such milk product which was thought to be susceptible to at least partial loss of biological activity once ingested due to fragmentation of molecules such as growth factors. Moreover, by virtue of the process for its isolation, WGFE contains only low levels of immunoglobulins which, as described above, are thought to be important anti-inflammatory factors.

Nevertheless, the capacity of whey protein supplementation to provide a benefit to persons engaged in resistance exercise training has been reported to provide a benefit. Whey protein isolate (WPI) and milk protein isolate (MPI), each having a different composition to whey growth factor extract, have been reported to be effective with bodybuilders in rapidly gaining lean muscle mass while reducing body fat. WPI is high in branched-chain amino acids and considered to be fast-acting, whereas MPI is mainly casein which is more slowly metabolised and is effective in promoting muscle growth. The use of WPI, or whey protein concentrate, in combination with the amino acids glutamine, leucine, isoleucine and valine to improve muscular fatigue in a rat model is the subject of WO 2004/049830 A1 (Tsuchita H et al.). The authors measured Tyrosine release from soleus muscle as the indicator of fatigue.

Figure 7:
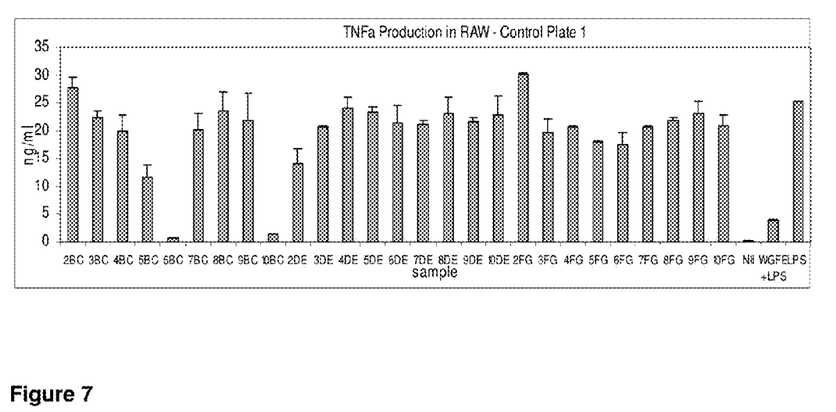
FIG. 7: TNF-alpha production (ng/ml) by RAW cells exposed to lipopolysaccharide (LPS) and cultured in the presence of colostrum (sample 2BC), WPI (sample 4BC) at 100 mg/ml, WGFE (sample 6BC) at 100 mg/ml, various milk fractions, or LPS alone (control). WGFE and LPS were also added to the culture simultaneously (sample WGFE+LPS). The values plotted represent the arithmetic mean±SEM of the average response obtained in 3 independent experiments.

The present inventors have found that a composition comprising whey growth factor extract altered the expression of genes involved in exercise-induced muscle inflammation and was 40 fold more effective than colostrum at inhibiting LPS-induced production of the pro-inflammatory cytokine TNF-alpha in an in vitro model of inflammation (See FIG. 7 and Example 2). In a separate study conducted by the inventors, trained athletes administered whey growth factor extract reported a reduction in post-exercise soreness. Importantly, in terms of the invention, whey growth factor extract may be isolated from normal bulk milk products without a requirement to maintain cows in a hyperimmune state or to harvest colostrum which is in limited supply relative to other milk products.

SUMMARY OF THE INVENTION

The invention relates to a WGFE composition and method of using the composition which enables persons undergoing resistance exercise training to reduce their level of muscle inflammation over that obtained with compositions of the prior art.

It is thus an object of the present invention to provide a composition and method of using same which is improved/more efficacious than compositions of the prior art for reducing muscle inflammation.

According to one aspect of the invention, there is provided a skeletal muscle inflammation-reducing composition comprising whey growth factor extract, isolated from a milk product by cation exchange chromatography.

In a further aspect of the invention, there is provided a muscle anti-inflammatory composition comprising whey growth factor extract, isolated from a milk product by a process comprising the steps;

a) applying the milk product to a SP Sepharose cation exchange column, b) washing the column with a buffer of low ionic strength, c) eluting the WGFE fraction with a buffer containing in the range 0.4-0.5M NaCl, or equivalent ionic strength, at pH 6.5.

According to another aspect of the invention, there is provided a muscle anti-inflammatory composition comprising whey growth factor extract, isolated from a milk product by a process comprising the steps;

a) applying the milk product to a SP Sepharose cation exchange column, b) washing the column with a buffer of 0.008M NaCl or less, c) eluting the WGFE fraction with a buffer containing 0.4M NaCl, or equivalent ionic strength, at pH 6.5.

In a further aspect of the invention, there is provided a composition according to the above wherein the whey growth factor extract is isolated from a milk product selected from whole milk, cheese whey, rennet casein whey, acid casein whey, or concentrates thereof, or skim milk.

In a further aspect of the invention, there is provided a composition according to the above when used as a muscle anti-inflammatory agent.

In a further aspect of the invention there is provided a method of reducing skeletal muscle inflammation in subjects undertaking resistance exercise training comprising administering to the subjects an efficacious amount of a composition comprising whey growth factor extract.

In a further aspect of the invention there is provided a method of reducing skeletal muscle inflammation in subjects undertaking resistance exercise training comprising administering to the subjects an efficacious amount of a composition comprising whey growth factor extract, isolated from a milk product by a process comprising the steps;

a) applying the milk product to a SP Sepharose cation exchange column, b) washing the column with a buffer of low ionic strength, c) eluting the WGFE fraction with a buffer containing in the range 0.4-0.5M NaCl, or equivalent ionic strength, at pH 6.5.

In a further aspect of the invention there is provided a method of reducing skeletal muscle inflammation in subjects undertaking resistance exercise training comprising administering to the subjects an efficacious amount of a composition comprising whey growth factor extract, isolated from a milk product by a process comprising the steps;

a) applying the milk product to a SP Sepharose cation exchange column, b) washing the column with a buffer of 0.008M NaCl or less, c) eluting the WGFE fraction with a buffer containing 0.4M NaCl, or equivalent ionic strength, at pH 6.5.

In another aspect of the invention there is provided a method of reducing skeletal muscle inflammation in subjects undertaking resistance exercise training wherein the amount of whey growth factor extract administered, per daily dose, is at least 5 mg/kg body weight to 12.5 mg/kg body weight. Preferably the daily dose of whey growth factor extract is at least 25 mg/kg body weight.

In a further aspect of the invention there is provided a use of whey growth factor extract, isolated from a milk product by cation exchange chromatography, for the production of a medicament for the treatment of a subject in need of reduced skeletal muscle inflammation.

In a further aspect of the invention there is provided a use of whey growth factor extract, isolated from a milk product by a process described above, for the production of a medicament for the treatment of a subject in need of reduced skeletal muscle inflammation.

According to another aspect of the invention, there is provided a skeletal muscle inflammation-reducing composition comprising whey growth factor extract, isolated from a milk product by cation exchange chromatography, and an additional protein source.

According to a further aspect of the invention the additional protein source is whey protein, preferably whey protein isolate (WPI), more preferably whey protein isolate wherein the whey protein isolate comprises:

| | |
|---|---|
| Moisture | 5.0% |
| Fat | 0.5% |
| pH (5% solution) | 6.3 |
| Ash | 3.7% |
| Lactose | 0.5% |
| Protein (TN x 6.38) | 90.0% |
| Sodium | 0.7% |
| Phosphorous | 0.3% |
| Calcium | 0.15% |

In a further aspect of the invention there is provided a method of reducing skeletal muscle inflammation in a subject undertaking resistance exercise training comprising administering to the subject an efficacious amount of a composition comprising whey growth factor extract and an additional protein source, such as whey, preferably WPI.

In a further aspect of the invention there is provided a method of reducing muscle inflammation in a subject undertaking resistance exercise training comprising administering to the subject a composition comprising an effective amount of whey growth factor extract, isolated from a milk product by cation exchange chromatography, and an additional protein source taken separately.

Preferably the amount of additional protein source administered, per daily dose, is at least 225 mg/kg body weight (dry weight) and preferably at least 435 mg/kg body weight (dry weight).

In a further aspect of the invention the administration of the composition of the invention is once per two or three days up to at least once per day, preferably before and/or immediately after resistance exercise training, more preferably immediately after resistance exercise training, most preferably between 20 minutes and two hours after exercise.

In a further aspect of the invention there is provided a use of whey growth factor extract, isolated from a milk product by cation exchange chromatography, and an additional protein source for the production of a medicament for the treatment of a subject in need of reduced skeletal muscle inflammation.

In a further aspect of the invention, there is provided a food or drink comprising the composition of the invention for use in a method to reduce skeletal muscle inflammation in a subject undertaking resistance exercise training.

In yet a further aspect of the invention there is provided a use of the composition of the invention for the manufacture of a food or drink to reduce skeletal muscle inflammation in a subject undertaking resistance exercise training.

DETAILED DESCRIPTION OF THE INVENTION

The invention relates to a composition containing WGFE and uses thereof to enable a subject undergoing resistance exercise training to reduce their level of muscle inflammation over that obtained with compositions of the prior art.

According to one aspect of the invention, there is provided a skeletal muscle inflammation-reducing composition comprising whey growth factor extract, isolated from a milk product by cation exchange chromatography.

The whey growth factor extract for use in the invention may be isolated from milk, skim milk, milk derivatives, whey, colostrum, and colostrum derivatives by, for example, the method described in Australian Patent No. 645589 (PCT/AU91/00303) which is incorporated herein by reference. This method essentially relies on strong cation exchange chromatography to selectively extract basic proteins from the starting material to constitute whey growth factor extract.

Process for Producing WGFE Fraction

A preferred method of producing WGFE for use in the invention is to use a column packed with SP (sulphopropyl) Sepharose To the column a flow of a dairy product, preferably skimmed milk, is applied until the volume of milk applied is up to 1000 times the volume of the resin packed into the column. The milk remaining in the column is removed with a buffer of low ionic strength (<0.008M NaCl or equivalent) for 10 min. The WGFE fraction is eluted from the column with a buffer containing sodium ions equivalent to 0.4-0.5M NaCl (though other cations would be suitable), most preferably 0.4M NaCl.

The mobile phase may have a pH within a broad range, such as 4.5-9.0, preferably 5.5-7.5, most preferably about 6.5. At the upper and lower limits both protein stability and the ability of proteins to bind to the cation exchange resin become influenced. A pH in the range 5.5-7.5 provides the highest WGFE yields.

The type of cation exchange resin suitable for adsorption of the WGFE components may include resins such as Sepharose cation exchange resin beads. For example, SP Sepharose Big Beads and CM Sepharose beads (products of GE Healthcare) which contain sulfopropyl functional groups and carboxymethyl groups, respectively, are suitable. The size of the cation exchange resin beads is preferably in the range from 45-300 μm. Both SP Sepharose beads in the range 45-165 μm and in the range 100-300 μm are suitable for WGFE purification according to the invention.

One of the further treatments to which the WGFE fraction can be subjected is desalting by, for example, dialysis or ultrafiltration.

Accordingly, in a further aspect of the invention, there is provided a composition according to the above wherein the whey growth factor extract is isolated from whey or skim milk. The whey used as starting material may be cheese whey, rennet casein whey, acid casein whey, or concentrates thereof. The amounts of whey growth factor extract and protein source to use according to the invention are to be sufficient for reduced muscle inflammation or to have a therapeutic effect.

In another aspect of the invention there is provided a dosage regime wherein the amount of whey growth factor extract administered, per daily dose, is at least 5 mg/kg body weight to 12.5 mg/kg body weight. Preferably the daily dose of whey growth factor extract is at least 25 mg/kg body weight.

In a further aspect of the invention there is provided a method of reducing skeletal muscle inflammation in subjects undertaking resistance exercise training comprising administering to the subjects an efficacious amount of a composition comprising whey growth factor extract.

When the composition includes an additional protein source, which may be any protein source suitable for consumption such as WPI, post-exercise inflammation is reduced compared to subjects administered a protein source alone. The protein source may be obtained from whole milk, preferably whey protein and more preferably whey protein isolate (WPI). One such whey protein isolate is available commercially under the trade name NatraPro™ by Murray Goulburn Co-Op Company Ltd. A typical composition of NatraPro™ WPI includes:

| | |
|---|---|
| Moisture | 5.0% |
| Fat | 0.5% |
| pH (5% solution) | 6.3 |
| Ash | 3.7% |
| Lactose | 0.5% |
| Protein (TN x 6.38) | 90.0% |
| Sodium | 0.7% |
| Phosphorous | 0.3% |
| Calcium | 0.15% |

Preferably the composition according to the invention also contains a protein source and, in a dosage regime, the amount of additional protein source per daily dose administered is at least 225 mg/kg body weight (dry weight) and preferably at least 435 mg/kg body weight (dry weight). The additional protein source could be formulated with the WGFE composition or formulated to be administered separately to the WGFE composition.

In a further aspect of the invention there is provided a use of whey growth factor extract for the production of a medicament for the treatment of a subject in need of reduced skeletal muscle inflammation. For example, athletes may require resistance exercise training to build up their muscle strength to enhance their performance, or to overcome a debilitating injury which has caused muscle wasting. The muscle inflammation may be caused by, for example, a 'corked' thigh, or a torn muscle. A medicament comprising the composition of the invention may further assist in the subject recovering more rapidly to return to their training regime and/or to compete. Muscle inflammation may also occur in those with a propensity for bruising, such as the elderly.

In a further aspect of the invention there is provided a method of reducing skeletal muscle inflammation in subjects undertaking resistance exercise training comprising administering to the subjects an efficacious amount of a composition comprising whey growth factor extract and an additional protein source.

It will be apparent to those skilled in the art that the administration of the composition of the invention may be on the days of training or on the days of training and/or other days, providing the regimen of administration results in reduced skeletal muscle inflammation. Preferably administration is on the days of exercise and more preferably administration occurs either just before and/or immediately after the exercise. More preferably, administration occurs between 20 minutes and 2 hours after exercise. Accordingly, in a preferred aspect of the invention, there is provided a method as described above wherein the administration is immediately after the exercise. Subjects administered 1 g WGFE plus 20 g WPI, or 2 g WGFE plus 20 g WPI immediately after resistance exercise training showed increased modulation of the expression of genes involved in inflammation compared to subjects administered WPI alone (see Examples and Results). In addition, subjects administered WGFE reported reduced post-exercise soreness compared to those administered WPI, supporting a role for WGFE in reducing post-exercise muscle inflammation.

Moreover, the composition of the invention may be used to reduce muscle inflammation in non-human mammals such as horses, greyhounds and others in which reduced muscle inflammation is desirable.

In a further aspect of the invention, there is provided a food or drink comprising the composition of the invention for use in a method to reduce skeletal muscle inflammation in subjects undertaking resistance exercise training.

In yet a further aspect of the invention there is provided a use of the composition of the invention for the manufacture of a food or drink to reduce skeletal muscle inflammation in subjects undertaking resistance exercise training.

WPI typically contains about 90% w/v protein; therefore 20 g of WPI contains about 18 g of protein as a nutritional source.

Whey growth factor extract typically contains about 85% w/v protein; therefore 2 g of whey growth factor extract contains about 1.7 g of protein as a nutritional source.

It will be appreciated that the present invention described herein is not to be limited to specific examples of features disclosed.

EXAMPLES

Example 1

Clinical Trial

A clinical trial was conducted in which 20 young males participated in a three month randomised double-blinded resistance training program. Whey growth factor extract was prepared according to the method broadly described in Australian Patent No. 645589 (PCT/AU91/00303), more specifically described_supra. Each whey protein formulation contained an artificial sweetener (Nutrasweet™, Nutrasweet Company, USA). Whey protein formulations were consumed immediately after each exercise session, with each subject completing three supervised exercise sessions per week.

Subjects were randomly assigned to one of three supplement groups:

Group A: 20 g NatraPro (WPI) per dose; n=7
Group B1: 20 g NatraPro (WPI) plus 1 g WGFE per dose; n=6
Group B2: 20 g NatraPro (WPI) plus 2 g WGFE per dose; n=7

A typical composition of NatraPro™ WPI includes:

| | |
|---|---|
| Moisture | 5.0% |
| Fat | 0.5% |
| pH (5% solution) | 6.3 |
| Ash | 3.7% |
| Lactose | 0.5% |
| Protein (TN x 6.38) | 90.0% |
| Sodium | 0.7% |
| Phosphorous | 0.3% |
| Calcium | 0.15% |

Muscle Analysis

Muscle samples were collected from the vastus lateralis muscle of the right leg using the percutaneous needle biopsy technique. Excised muscle tissue was visually inspected, dissected free of any fat or connective tissue and blotted to remove excess blood and immediately frozen in liquid nitrogen for subsequent analysis. A portion of the muscle tissue was mounted in an aqueous mounting medium and frozen in isopentane cooled in liquid nitrogen for subsequent immunohistochemical analysis.

Immunohistochemistry

Serial sections (10 m) of each sample were mounted on microscope slides for analysis of myosin heavy chain fibre type. An immunohistochemical technique based on the fast and slow isoforms of myosin was used to examine fibre type distribution and muscle cross-sectional area based on the protocol of Behan. Cellular localisation of proteins was performed using standard immunohistochemical techniques and antibodies raised against the proteins of interest.

RNA Extraction & Gene Expression Analysis

RNA was extracted from skeletal muscle samples using the ToTALLY RNA kit and reagents (Ambion Inc.) according to the manufacturer's instructions. Total RNA concentrations and quality were determined using the Agilent 2100 Bioanalyzer (Agilent Technologies, Inc.). Subsequently, RNA was reverse transcribed into cDNA using the AMV reverse transcriptase kit protocols and reagents (Promega). Analysis of gene expression was performed on the Applied Biosystems 7500 Real-Time PCR System using gene specific primers designed using Primer Express 2.0 software.

Protein Expression Analysis

Standard western blotting techniques and an antibody directed towards a common section of myosin heavy chain protein isoforms (Zymed) was employed to examine total Myosin Heavy Chain protein content.

Results

Results are presented as mean±SEM and significance calculated by two-way ANOVA using Bonforoni post hoc tests. No significant differences in age, weight, height, or BMI values were observed both pre and post training.

TABLE 1

| | Subject Characteristics | | |
|---|---|---|---|
| Subject Characteristics | NatraPro WPI (A) (n = 7) | NatraPro WPI (B 1) (n = 6) | NatraPro WPI (B 2) (n = 7) |
| Age | 20.4 ± 0.6 | 19.5 ± 0.6 | 19.0 ± 0.4 |
| Height | 182.7 ± 3.3 | 180 ± 5.2 | 182.3 ± 4.1 |
| Weight | | | |
| Pre Training | 79.9 ± 4.0 | 80.3 ± 4.6 | 79.3 ± 6.0 |
| Post Training | 80.1 ± 3.2 | 80.0 ± 4.7 | 80.9 ± 5.9 |
| BMI | | | |
| Pre Training | 24.5 ± 0.8 | 24.3 ± 1.0 | 23.9 ± 1.1 |
| Post Training | 24.07 ± 1.1 | 24.2 ± 1.0 | 24.4 ± 1.0 |

Gene Expression Analysis

Figure 1:
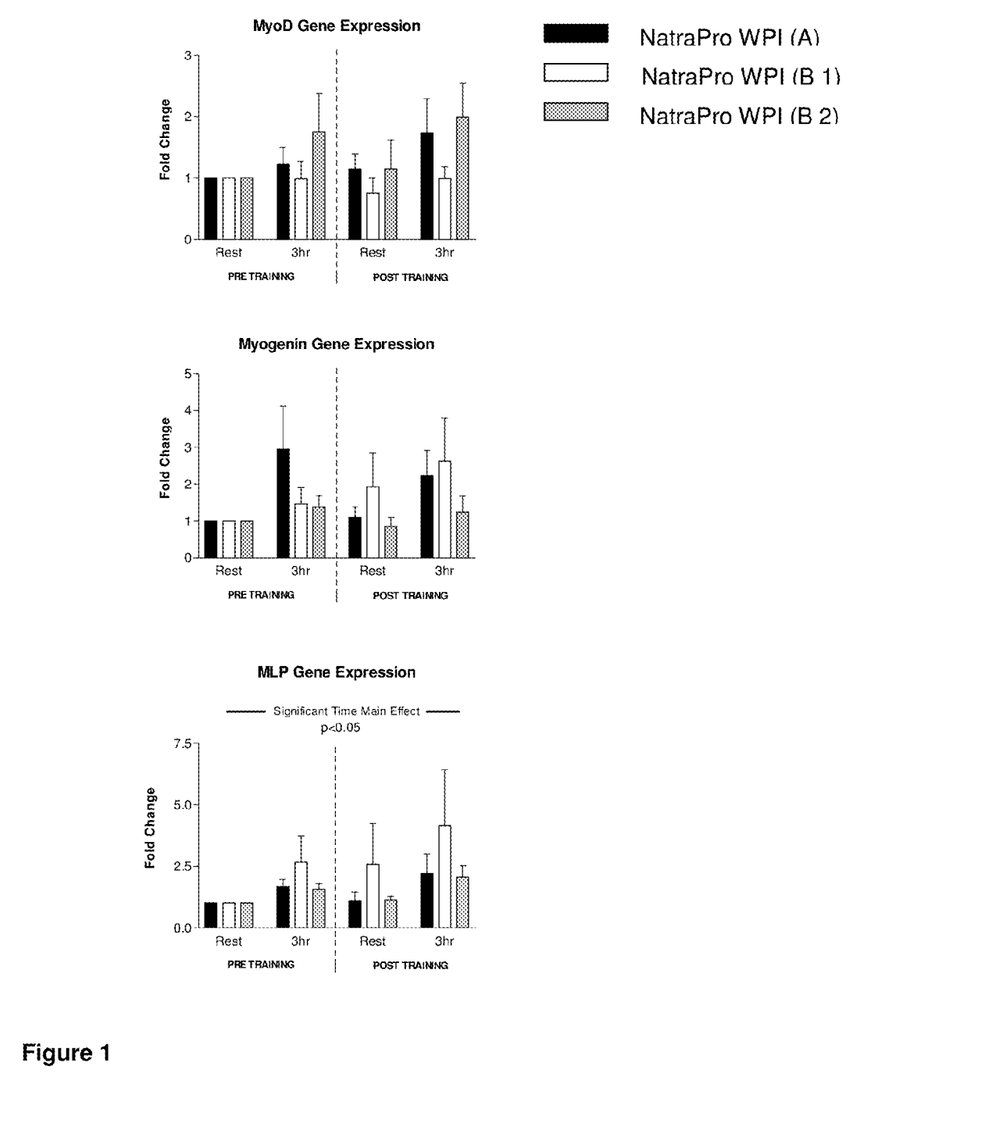
FIG. 1: Fold change in Myo D, myogenin, and myostatin gene (mRNA) expression in the vastus lateralis muscle of adult subjects, at rest and following 3 hours of resistance exercise training performed at the start of the trial [pre-training] and following 12 weeks of treatment [post-training] with 20 g WPI (Group A), 1 g WGFE+20 g WPI (Group B1), or 2 g WGFE+20 g WPI (Group B2). Results are presented as mean±SEM.
Figure 2:
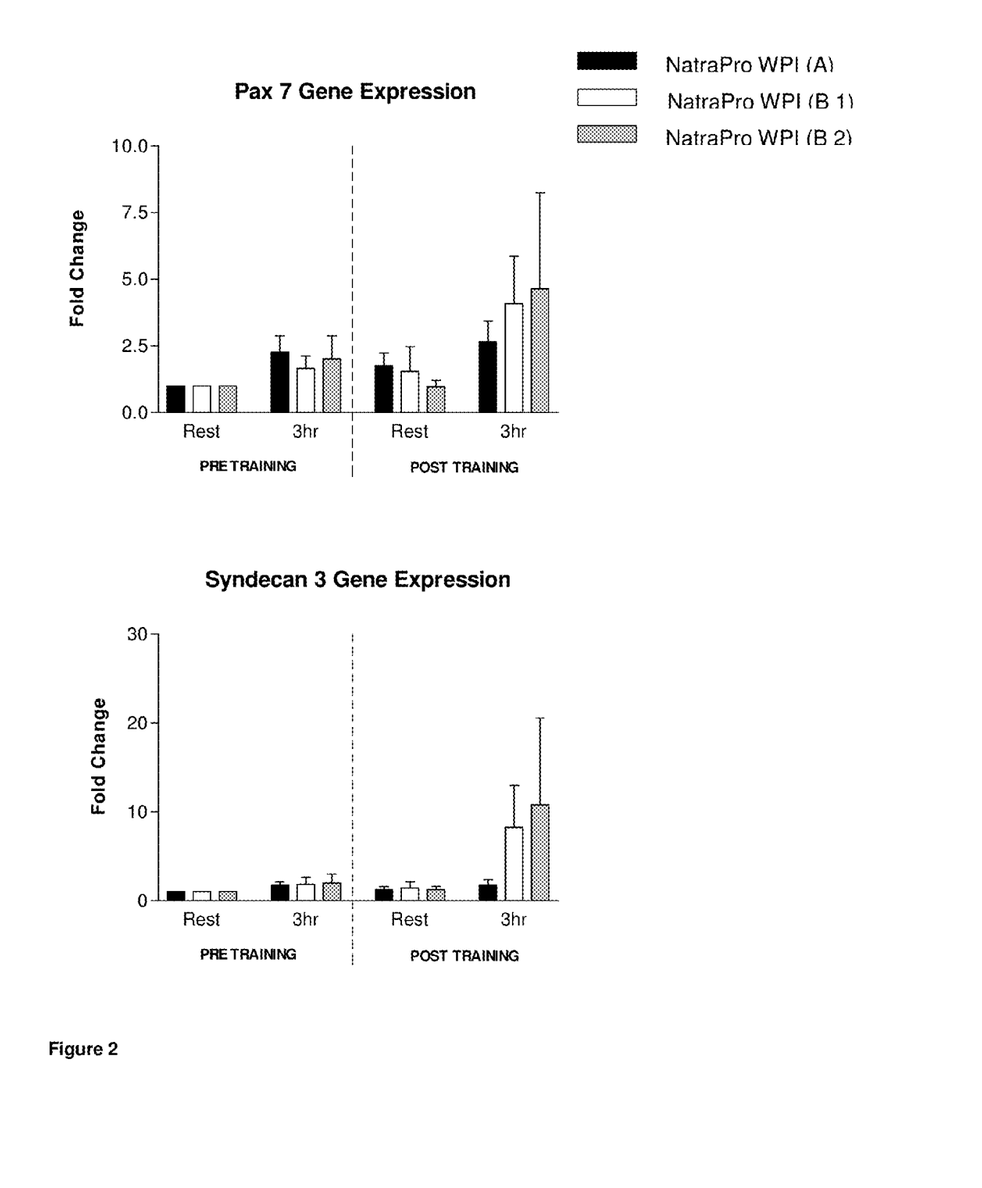
FIG. 2: Fold change in Pax 7 and Syndecan 3 gene (mRNA) expression in the vastus lateralis muscle of adult subjects, at rest and following 3 hours of resistance exercise training performed at the start of the trial [pre-training] and following 12 weeks of treatment [post-training] with 20 g WPI (Group A), 1 g WGFE+20 g WPI (Group B1), or 2 g WGFE+20 g WPI (Group B2). Results are presented as mean±SEM.
Figure 3:
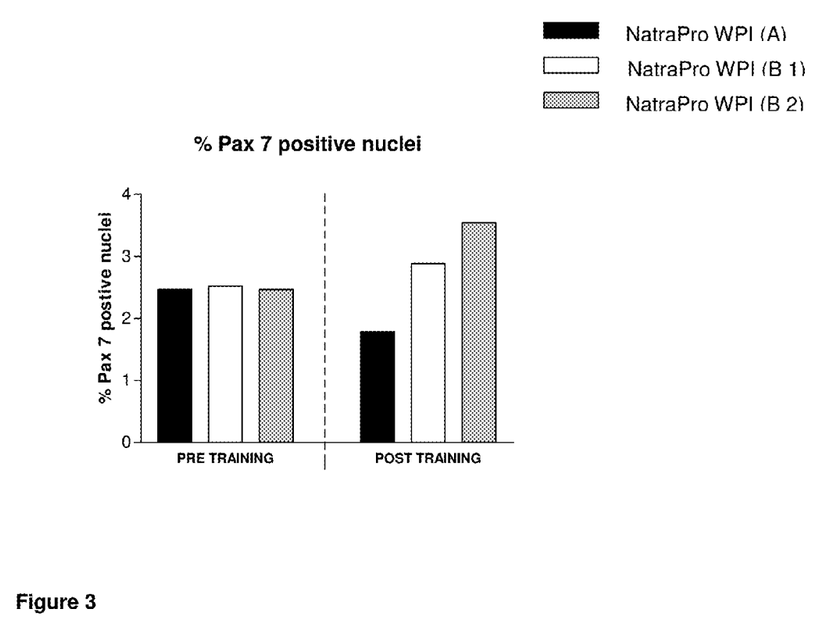
FIG. 3: Percentage of Pax 7 positive nuclei in tissue sections from the vastus lateralis muscle of adult subjects, following 3 hours of resistance exercise training performed at the start of the trial [pre-training] and following 12 weeks of treatment [post-training] with 20 g WPI (Group A), 1 g WGFE+20 g WPI (Group B1), or 2 g WGFE+20 g WPI (Group B2) as analysed by immunohistochemical staining.
Figure 4:
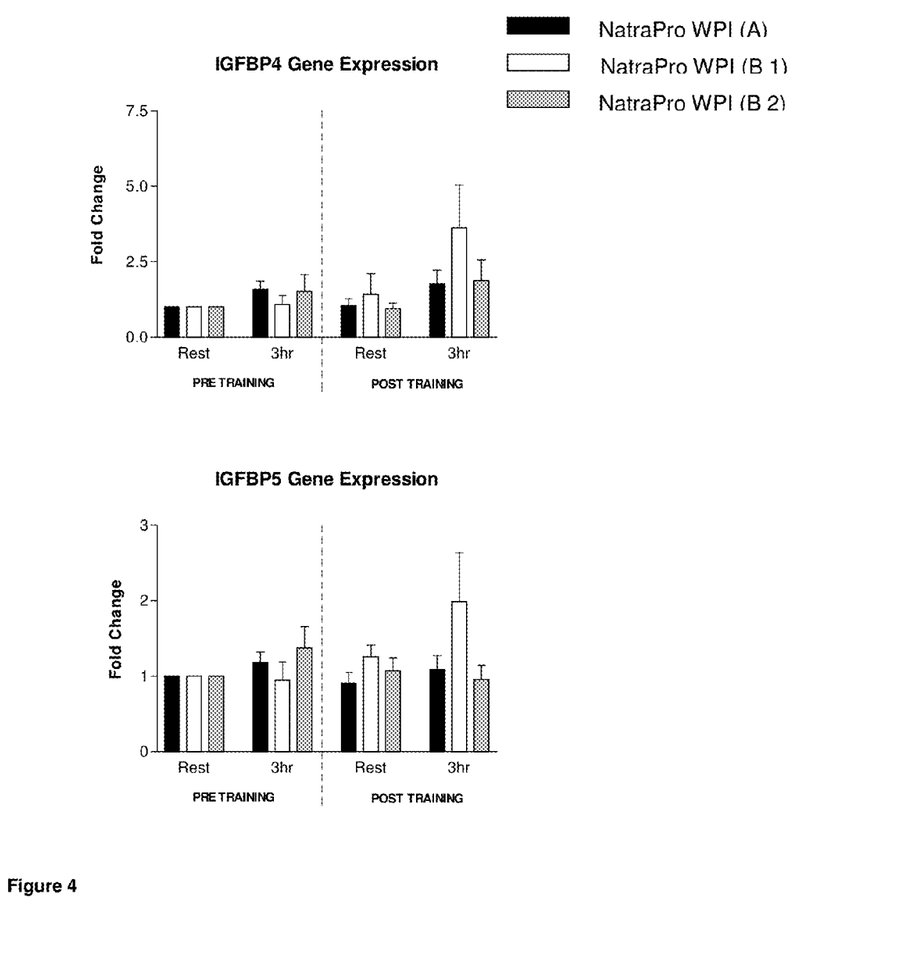
FIG. 4: Fold change in IGF-1 Binding Protein 4 and 5 gene (mRNA) expression in the vastus lateralis muscle of adult subjects, at rest and following 3 hours of resistance exercise training performed at the start of the trial [pre-training] and following 12 weeks of treatment [post-training] with 20 g WPI (Group A), 1 g WGFE+20 g WPI (Group B1), or 2 g WGFE+20 g WPI (Group B2). Results are presented as mean±SEM.
Figure 5:
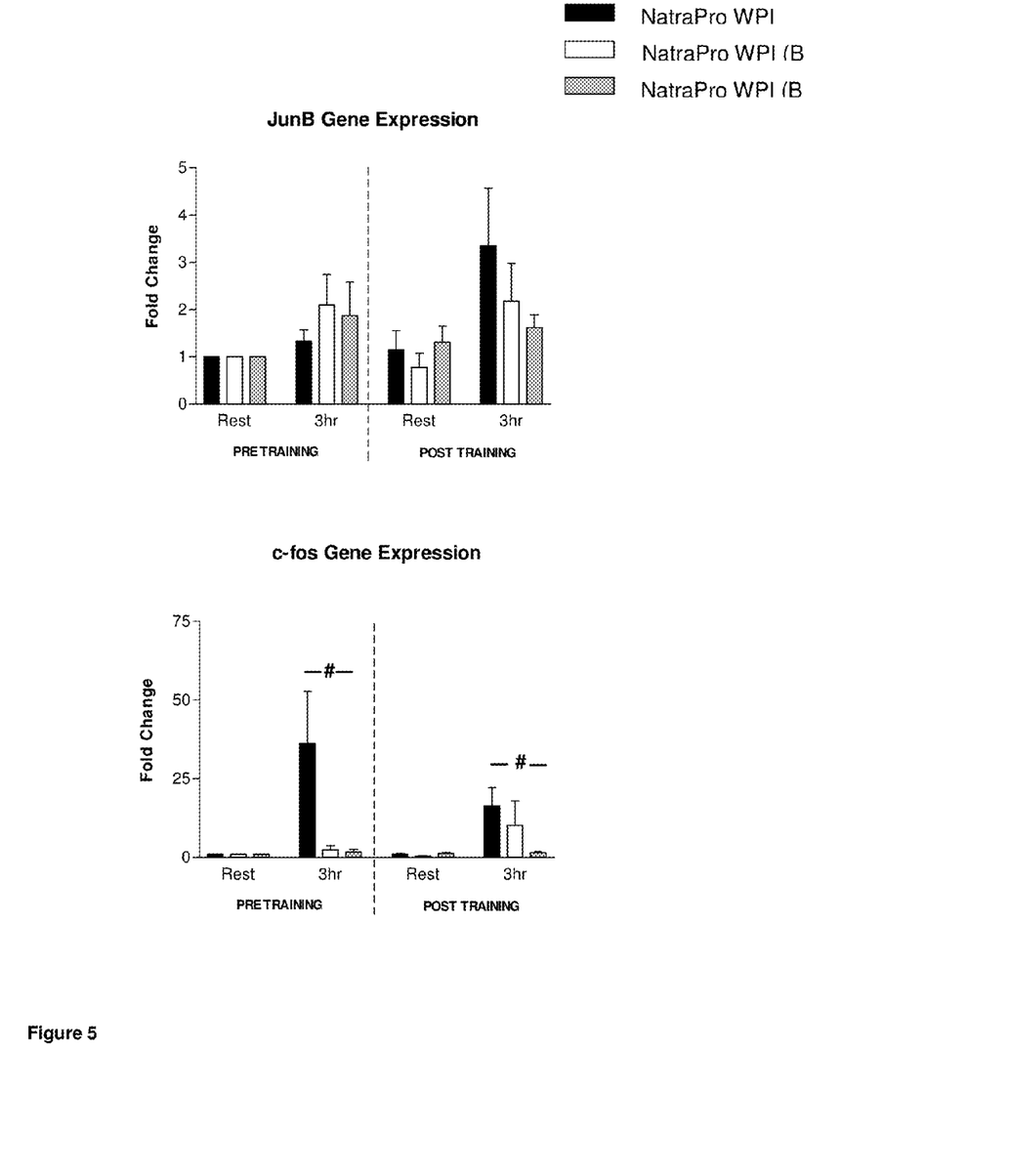
FIG. 5: Fold change in Jun B and c-fos gene (mRNA) expression in the vastus lateralis muscle of adult subjects, at rest and following 3 hours of resistance exercise training performed at the start of the trial [pre-training] and following 12 weeks of treatment [post-training] with 20 g WPI (Group A), 1 g WGFE+20 g WPI (Group B1), or 2 g WGFE+20 g WPI (Group B2). Results are presented as mean±SEM.
Figure 6:
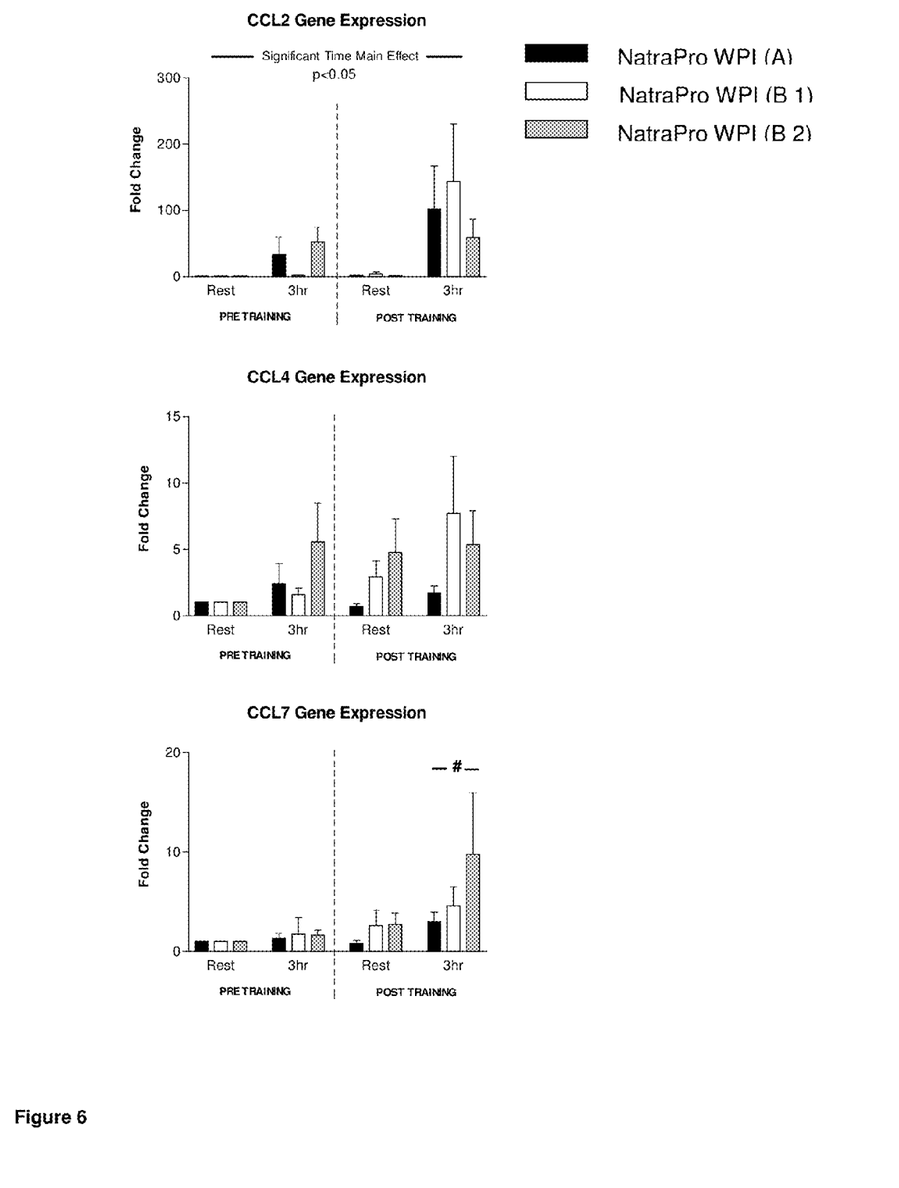
FIG. 6: Fold change in CCL2, 4 and 7 gene (mRNA) expression in the vastus lateralis muscle of adult subjects, at rest and following 3 hours of resistance exercise training performed at the start of the trial [pre-training] and following 12 weeks of treatment [post-training] with 20 g WPI (Group A), 1 g WGFE+20 g WPI (Group B1), or 2 g WGFE+20 g WPI (Group B2). Results are presented as mean±SEM.

There was no observed, consistent effect of training or treatments on the expression of MyoD and myogenin whilst training significantly increased the expression of muscle LIM protein (MLP) (FIG. 1). The expression of Pax 7 and Syndecan 3, two markers of satellite cell recruitment and proliferation, was increased 2-fold and 7-fold, respectively, following 12 weeks of training and is supported by protein expression data (FIGS. 2 and 3). The expression of IGFBP4 and IGFBP5 (FIG. 4) were markedly increased in group B1 at 12 weeks in response to acute exercise. The normal post-exercise up-regulation of the early response genes jun-B and c-fos which are linked to muscle inflammation (Chen Y W et al., J. App. Physiol. 2003; 95(6):2485-94) was attenuated in both B1 and B2 supplement groups suggesting a reduced stress response in these groups (FIG. 5). At 12 weeks both the resting and post-exercise expression levels of CCL4 and CCL7 were increased following a single bout of resistance exercise in groups B1 and B2 (significantly) compared with control group A (FIG. 6).

Example 2

Effect of WGFE on LPS-Induced TNF-Alpha Expression by Raw Cells

Figure 8:
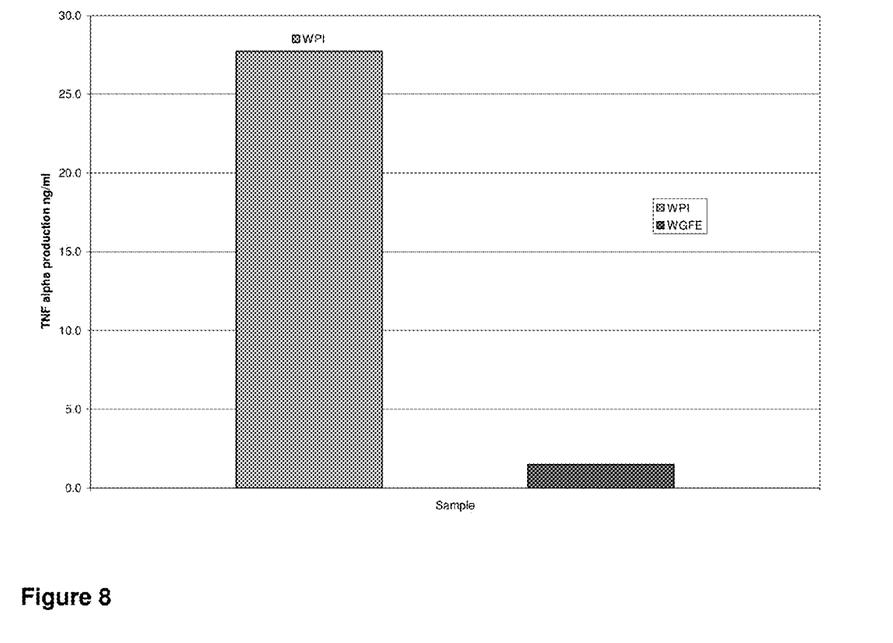
FIG. 8: Comparison of TNF-alpha production (ng/ml) by RAW cells exposed to lipopolysaccharide (LPS) and cultured in the presence of 100 mg/ml WPI or 100 mg/ml WGFE.

An in vitro study was conducted to test the effect of various milk product fractions on LPS-induced pro-inflammatory TNF-alpha expression by RAW cells. RAW cells were grown in the presence of LPS and then colostrum (sample 2BC), WPI (sample 4BC) at 100 mg/ml, WGFE (sample 6BC) at 100 mg/ml, or various milk fractions were added at 100 mg/ml. In one sample no milk product was added following LPS stimulation ('+ve' control; 'LPS'). WGFE and LPS were also added to the culture simultaneously (sample WGFE+LPS). The values plotted represent the arithmetic mean±SEM of the average response obtained in 3 independent experiments (FIG. 7). LPS alone stimulated the production of 25.3 ng/ml TNF-alpha; which was not reduced by colostrum (27.7 ng/ml), but was surprisingly reduced to 0.7 ng/ml by WGFE, which is 3% of the +ve control LPS-induced level and 2.5% of the colostrum sample level. A comparison was done between the effect of WGFE and WPI on inhibition of LPS-induced TNF-alpha expression in RAW cells (FIG. 8), which shows that WGFE decreased TNF-alpha production by 94% compared to the equivalent amount of WPI.

Whey growth factor extract was prepared as for Example 1.

The data supports that WGFE reduces the inflammation response in muscle following resistance exercise training. In vitro data suggests that WGFE reduces inflammation by inhibiting TNF-alpha expression. The data also supports that WGFE in combination with an additional protein source such as WPI decreases the post-exercise inflammatory response to a greater extent than observed when WPI, a protein source known to be used by subjects undertaking resistance exercise training, is administered alone.

The invention claimed is:

1. A method of reducing resistance training induced muscle inflammation in a subject, undergoing resistance training, in need thereof comprising:
    administering to the subject an effective amount of a composition comprising at least 5 mg/kg body weight of whey growth factor extract (WGFE), wherein the WGFE is isolated from a bovine milk product selected from the group consisting of cheese whey, rennet casein whey, acid whey and skim milk, and wherein the WGFE is obtained by:
    a) applying the bovine milk product to cation exchange resin beads containing sulfopropyl functional groups;
    b) washing the cation exchange resin beads with a buffer of low ionic strength; and
    c) eluting and isolating the WGFE from the cation exchange resin beads with a buffer containing 0.4-0.5M NaCl at pH 6.5.

2. The method of claim 1, wherein the composition further comprises an additional protein.

3. The method of claim 1, further comprising administering protein separately from the composition.

4. The method of claim 2, wherein the composition comprises protein in an amount of at least 225 mg/kg body weight.

5. The method of claim 3, wherein the protein is administered in an amount of at least 225 mg/kg body weight.

6. The method of claim 2, wherein the protein is whey protein.

7. The method of claim 3, wherein the protein is whey protein.

8. The method of claim 1, wherein the composition is administered to the subject between 20 minutes and two hours after resistance training.

9. The method of claim 1, wherein the composition comprising whey growth factor extract is in the form of a food, drink, tablet or capsule.

10. The method of claim 1, wherein the composition is in the form of a nutritional bar or snack food.

11. The method of claim 1, wherein the bovine milk product is skim milk.

12. The method of claim 1, wherein the composition comprises whey growth factor extract in an amount of at least 12.5 mg/kg body weight.

13. The method of claim 1, wherein the composition comprises whey growth factor extract in an amount of at least 25 mg/kg body weight.

14. The method of claim 1, wherein the muscle is skeletal muscle.

15. The method of claim 1, wherein the subject has muscle wasting or is an athlete.

16. The method of claim 1, wherein the subject is a non-human mammal.

17. The method of claim 1, wherein the subject is a horse or greyhound.

18. The method of claim 1, wherein the subject is a human.

* * * * *